United States Patent [19]

Heavner et al.

[11] 4,198,974

[45] Apr. 22, 1980

[54] COMBINATION STOPPER FOR USE IN MEDICAL AND CHEMICAL SAMPLING OR TESTING

[75] Inventors: Paul W. Heavner, Kettering, Ohio; Roger J. Woessner, Lindenhurst, Ill.; Susan E. Clifford, Bala-Cynwyd, Pa.

[73] Assignee: Baxter Travenol Laboratories, Inc., Deerfield, Ill.

[21] Appl. No.: 959,108

[22] Filed: Nov. 9, 1978

[51] Int. Cl.$^{2}$ .................... A61M 5/00

[52] U.S. Cl. .................... 128/215; 128/218 R; 215/355; 215/DIG. 3

[58] Field of Search .................... 128/215, 216, 218 R, 128/218 D, 218 DA, 218 M, 220, 221, 234, 224, 272, 272.1, 272.3, 765, 766, 764, 763; 215/247, 296, 300, 355, 228, 320, DIG. 3

[56] References Cited

U.S. PATENT DOCUMENTS

| | | | |
|---|---|---|---|
| 2,722,257 | 11/1955 | Lockhart | 128/765 X |
| 2,812,763 | 11/1957 | Ferguson | 128/218 R |
| 2,902,995 | 9/1959 | Loper | 128/215 |
| 3,087,638 | 4/1963 | Loper | 215/DIG. 3 |
| 3,181,529 | 5/1965 | Wilburn | 128/764 |
| 3,344,786 | 10/1967 | Berg et al. | 128/215 |
| 3,405,712 | 10/1968 | Pierick | 128/218 M |
| 3,734,079 | 5/1973 | Weber | 128/766 |
| 3,948,261 | 4/1976 | Steiner | 215/DIG. 3 |

*Primary Examiner*—John D. Yasko

*Attorney, Agent, or Firm*—Paul C. Flattery; John P. Kirby, Jr.; Gerald S. Geren

[57] ABSTRACT

There is disclosed herein a combination stopper for effecting an air-tight seal with the barrel of a syringe to protect the contents from contamination. The stopper is adapted for use with either the luer tip or a needle attached to the end of the syringe barrel. The stopper includes an elongated frustoconically-shaped main body portion having oppositely disposed end walls, and the end wall at the large-diameter end of the main body portion has a generally planar and continuous surface. An elongated frustoconically-shaped luer-receiving nipple is integrally formed with and extends from the small-diameter end wall of the main body portion, with the free end of the nipple being inwardly recessed. The luer-receiving nipple is shaped, sized and constructed to receive and seal the syringe luer tip. The stopper is formed of an elastomeric material having a durometer hardness of approximately 80 so as to provide an air-tight seal when the main body portion thereof is pierced by the syringe needle or when the luer-receiving needle is friction fit with the luer tip.

4 Claims, 4 Drawing Figures

FIG. 1
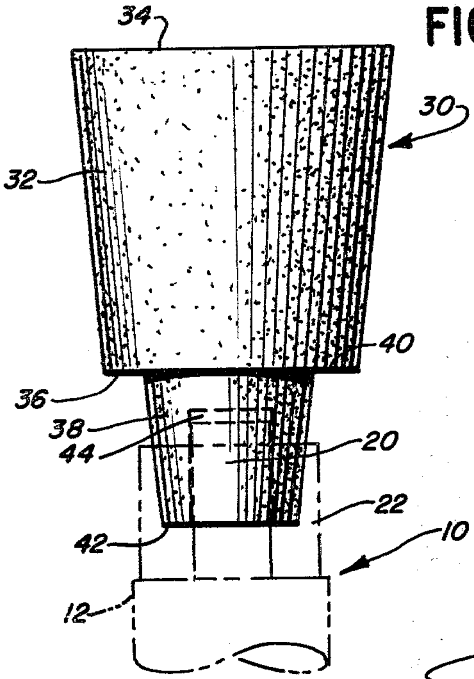
FIG. 2
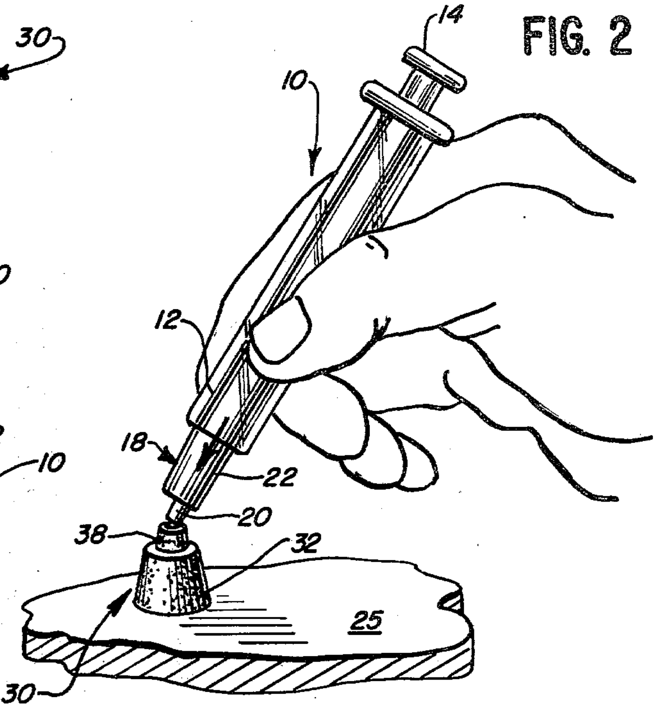
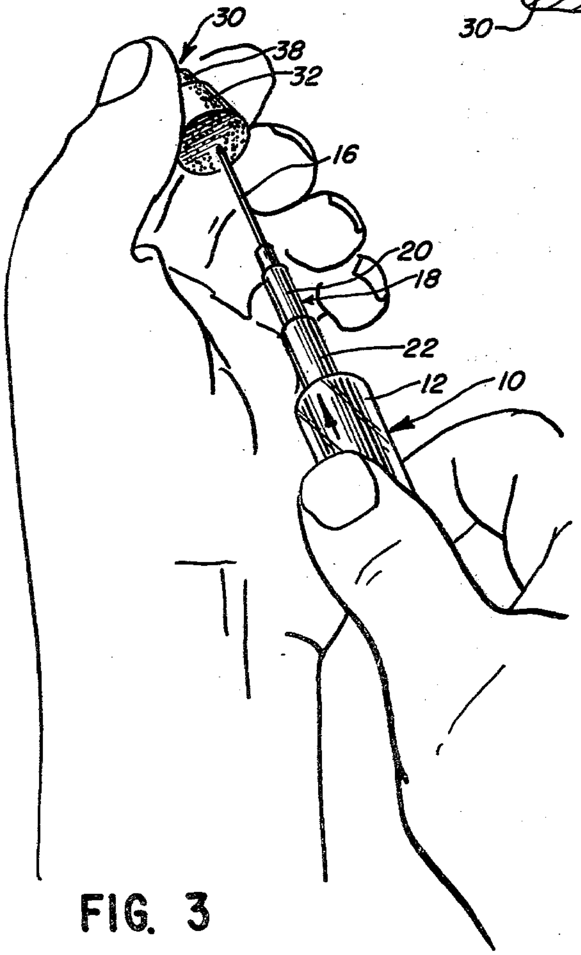
FIG. 3
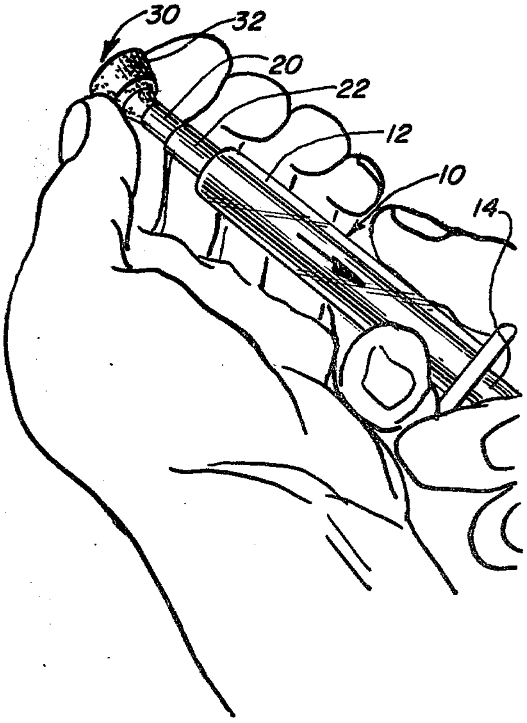
FIG. 4

COMBINATION STOPPER FOR USE IN MEDICAL AND CHEMICAL SAMPLING OR TESTING

FIELD OF THE INVENTION

This invention relates generally to a stopper element for a blood sampling syringe, and more particularly, to a combination stopper for effecting an air-tight seal used with either a luer or needle on a syringe.

BACKGROUND OF THE INVENTION

Syringes have been used to extract samples of blood and transfer the extracted blood to various types of testing apparatus for analysis. One particular type of analysis is the determination of blood gases commonly referred to as $pO_2$. The syringes are normally equipped with male luer tips to which needles may be attached, and depending upon the apparatus, the transfer is made using either the needle or luer tip.

When blood is transferred from a patient to the testing apparatus, it is essential to prevent contamination of the syringe.

Stoppers are commonly provided to frictionally cap the syringes so as to seal the contents thereof, thereby preventing contamination after sampling and during handling. Examples of syringe sealing stoppers can be found in U.S. Pat. Nos. 3,534,734, Budreck; 3,809,068, Kosowsky; 4,041,934, Genese; and 4,057,052, Kaufman et al.

While the stoppers of the prior art were especially adapted to seal either the luer tip of the syringe or the needle tip, no single stopper was adapted to serve the combined purpose of sealing both the luer tip of the syringe as well as the needle affixed to the luer-tipped syringe.

It is accordingly one object of the present invention to provide a combination stopper which will effect air-tight sealing of either a luer-tipped or a needle-tipped syringe.

While some prior stoppers attempted to provide seals for luer-tipped syringes, their effectiveness was hampered by: (1) difficulty in grasping the stopper body for securing and removing the stopper; (2) failure to effect an air-tight seal resulting in contaminated samplings and questionable test results; and/or (3) an inability to seal the syringe using only one hand.

It is therefore another object of the present invention to provide a combination stopper which is easy to grasp, is adapted to effect a secure, air-tight seal on the luer tip of the syringe and can be used in one-handed operation.

And while some prior stoppers attempted to provide ad adequate air-tight seal for needles attached to the luer-tipped syringes, the rigidity of the material from which the stoppers were fabricated hindered the entry of the needle into the body of the stopper.

It is still a further object of the present invention to provide a combination stopper fabricated from a material which facilitates needles entry into the stopper and yet effects air-tight sealing of the contents of the syringe.

These and other objects and features of advantage of the present invention, not at this time enumerated, will readily suggest themselves as the nature of the invention is better understood from a consideration of the detailed description.

SUMMARY OF THE INVENTION

There is disclosed herein a combination stopper which is adapted for sealing needle tipped and luer tipped syringes so as to prevent contamination of those syringes after sampling and during handling. The syringe includes an elongated, frustoconically-shaped main body portion having oppositely disposed end walls. The end wall at the large diameter end of the main body portion includes a generally planar and continuous surface for receiving the needle tipped syringe. Integrally formed with and extending from the small diameter end wall of the main body portion is an elongated, frustoconically-shaped luer-receiving nipple. The small diameter, or free end, of the nipple is inwardly recessed to engage a protruding sleeve from the luer-tipped syringe. The recessed nipple is shaped, sized and constructed to provide an air-tight seal when the luer tipped syringe is received in said recess. The stopper is fabricated of a material having a durometer hardness reading of about 80 so as to provide an air-tight seal when the main body portion thereof is pierced by the needle tipped syringe.

BRIEF DESCRIPTION OF THE DRAWINGS

In the accompanying single sheet of drawings, forming a part of the specification, one illustrative embodiment of the invention is illustrated.

In these drawings:

FIG. 1 is a side elevation view of the combination stopper of the present invention, showing the recessed luer-receiving nipple effecting an air-tight seal over the luer tip of a syringe which is illustrated in phantom;

FIG. 2 is a perspective view showing the stopper resting on a surface and a luer-tipped syringe being inserted into the recess in the nipple of the stopper;

FIG. 3 is a perspective view showing a needle tipped syringe being inserted into the body portion of the combination stopper of the present invention; and FIG. 4 is a perspective view showing the combination stopper of the present invention being removed from a luer-tipped syringe.

DESCRIPTION OF THE PREFERRED EMBODIMENT

Referring now to the drawings in detail, a hypodermic syringe is generally designated by the reference numeral 10 and includes four basic elements, namely, a cylindrical barrel 12, a plunger 14, a needle 16, and a luer 18. The luer 18 is secured to one end of the barrel 12 and includes an elongated inner sleeve 20 and an outer sleeve 22 spaced from the inner sleeve 20. The inner sleeve 20 communicates with the interior of the barrel 12 to form a passageway. The needle 16 is adapted to be attached to the luer 18 by frictionally engaging the exterior surface of the inner sleeve 20. The action of inserting or withdrawing the plunger 14 thereby causes the blood or other fluid being sampled to respectively exit from or be drawn into the barrel 12 of the syringe 10.

The combination stopper of this invention is referred to generally as 30 and includes an elongated, frustoconically-shaped main body portion 32 having oppositely disposed end walls 34 and 36 (see FIG. 1). The end wall 34 at the larger diameter end of the main body portion 32 is a generally planar and continuous surface.

Integrally formed with the main body portion 32 and extending from the small diameter end wall 36 thereof is an elongated, frustoconially-shaped luer-receiving nipple 38 having oppositely disposed end walls 40 and 42. The small diameter or "free" end wall 42 of the nipple 38 includes a luer sleeve-receiving recess 44.

As can be seen in FIG. 1, the luer-receiving nipple 38 is shaped, sized and constructed to provide an air-tight seal when the luer tip 18 of the syringe 10 is received in the recess 44. In other words, as the luer 18 of the syringe 10 is frictionally forced into the recess 44 in the nipple 38 of the stopper 30 (a process which can be accomplished with one hand, as shown in FIG. 2), the interior peripheral surface of the recess 44 contacts the exterior peripheral surface of the elongated inner sleeve 20. Simultaneously, the exterior peripheral surface of the nipple 38 contacts the interior peripheral surface of the outer sleeve 22. In this manner the leading, small diameter end of the nipple 38 is sandwiched between the inner sleeve 20 and the outer sleeve 22 of the luer 18. As force is continued to be applied in the direction of the arrow in FIG. 2, the nipple is moved more deeply into the space between the sleeves 20 and 22. The depth of insertion is limited either by the compressibility of the material from which the stopper 30 is fabricated or an ultimate stop is formed by the bottom wall of the recess 44.

The double seal, a first seal between the nipple 38 and the inner sleeve 20 and a second seal between the nipple 38 and the outer sleeve 22 seals the syringe 10 so that air cannot contaminate the contents of the barrel 12.

The stopper 30 is fabricated from a resiliently compressible elastomeric material having a durometer hardness reading of approximately 80. Such a material is easily penetrable when needle tipped syringe is thrust into the body portion 32 of the stopper 30 in the direction of the arrow depicted in FIG. 3. A material having the durometer reading of 80 further provides an air-tight seal about the opening in the distal end of the needle 16 to prevent contamination.

As is seen from FIGS. 3 and 4, the frustoconical shape of the main body portion 32 of the stopper 30 is particularly adapted to facilitate the grasping thereof. Further, because the large diameter end 34 of the main portion 32 is continuous, the stopper 30 is able to rest on a support surface, such as 25, to allow for one-handed insertion of the luer tip 18 of a syringe 10 into the stopper recess 44 or even the needle if necessary.

It is to be understood that the proportion and shape of the preferred embodiment may vary and still remain within the spirit and scope of this invention.

What is claimed is:

1. A combination stopper for sealing a luer-tipped or a needle-tipped syringe and adapted to effect air-tight sealing of the contents of the syringe, the stopper including:

an elongated, frustoconically-shaped main body portion having oppositely disposed end walls, the end wall at the larger diameter end of the main body portion having a generally planar and continuous surface;

an elongated, frustoconically-shaped luer-receiving nipple integrally formed with and extending from the small diameter end wall of the main body portion, with the free end of the nipple being inwardly recessed;

the luer-receiving nipple being shaped, sized and constructed to provide an air-tight seal when a luer-tipped syringe is received in said recess; and the stopper being formed of a material adapted to provide an air-tight seal when the main body portion thereof is pierced by a syringe needle.

2. A combintaion stopper for use with a syringe having a luer tip to seal either the luer tip or a needle attached to the luer tip, thereby preventing contamination of the contents of the syringe; the syringe including a cylindrical barrel having a luer tip at one end thereof, the luer tip defined by an elongated inner sleeve communicating with the interior of the cylindrical barrel to form a passageway therebetween, an outer sleeve spaced from and surrounding the inner sleeve, and a needle adapted to be secured to the luer tip; the stopper comprising, in combination:

an elongated main body portion having a first, generally planar and continuous end wall, and a second, oppositely disposed end wall;

an elongated luer-receiving nipple integrally formed with and extending from the second end wall, the free end of the luer-receiving nipple including an inwardly directed recess;

the luer-receiving nipple shaped, sized and constructed relative to the luer tip of the syringe to provide an air-tight seal when the elongated inner luer tip sleeve is inserted into the recess in the luer-receiving nipple; and the stopper being formed of a material adapted to be easily penetrable by the syringe needle while providing an air-tight seal when the main stopper body is pierced by the syringe needle.

3. A combination stopper as in claim 1, wherein the main body and the luer-receiving nipple are both generally frustoconically shaped with the large diameter end of the main body forming the continuous end wall.

4. A combination stopper as in claims 1 or 2, wherein the stopper is formed from a material having a durometer hardness reading approximately 80.

* * * * *